US00PP18344P2

(12) United States Plant Patent
Ghyselen

(10) Patent No.: US PP18,344 P2
(45) Date of Patent: Dec. 25, 2007

(54) ***BISTORTA* PLANT NAMED 'ORANGE FIELD'**

(50) Latin Name: *Bistorta amplexicaulis*
Varietal Denomination: Orange Field

(75) Inventor: Chris Ghyselen, Oedelem (BE)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/494,096

(22) Filed: Jul. 27, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent L. Bell
(74) *Attorney, Agent, or Firm*—C. A. Whealy

(57) ABSTRACT

A new and distinct cultivar of *Bistorta* plant named 'Orange Field', characterized by its upright and outwardly spreading plant habit; basal branching habit; freely flowering habit; and light red-colored flowers.

2 Drawing Sheets

Botanical designation: *Bistorta amplexicaulis.*
Cultivar denomination: 'Orange Field'.

BACKGROUND OF THE INVENTION

The present invention relates to a new and distinct cultivar of *Bistorta,* botanically known as *Bistorta amplexicaulis* and hereinafter referred to by the name 'Orange Field'.

The new *Bistorta* originated from an open-pollination in 2001 of an unnamed selection of *Bistorta amplexicaulis,* not patented, as the female, or seed, parent with an unknown selection of *Bistorta amplexicaulis,* as the male, or pollen, parent. The new *Bistorta* was discovered and selected by the Inventor as a single flowering plant from within the progeny of the stated open-pollination grown in a controlled environment in Oedelem (Beernem), Belgium during the summer of 2002.

Asexual reproduction of the new cultivar by softwood cuttings in Oedelem (Beernem), Belgium, since 2002, has shown that the unique features of this new *Bistorta* are stable and reproduced true to type in successive generations.

SUMMARY OF THE INVENTION

Plants of the cultivar Orange Field have not been observed under all possible environmental conditions. The phenotype may vary somewhat with variations in environment such as temperature and light intensity without, however, any variance in genotype.

The following traits have been repeatedly observed and are determined to be the unique characteristics of 'Orange Field'. These characteristics in combination distinguish 'Orange Field' as a new and distinct cultivar:

1. Upright and outwardly spreading plant habit.
2. Basal branching habit.
3. Freely flowering habit.
4. Light red-colored flowers.

Plants of the new *Bistorta* differ from plants of the female parent selection primarily in plant size and flower color.

Plants of the new *Bistorta* can be compared to plants of the *Bistorta* cultivar Blackfield, not patented. In side-by-side comparisons conducted by the Inventor in Oedelem (Beernem), Belgium, plants of the new *Bistorta* differed primarily from plants of the cultivar Blackfield in flower color as plants of the cultivar Blackfield had dark red-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Bistorta.*

The photograph on the first sheet comprises a side perspective view of typical flowering plants of 'Orange Field' grown in an outdoor nursery.

The photograph at the top of the second sheet is a close-up view of typical inflorescences of 'Orange Field'.

The photograph at the bottom of the second sheet is a close-up view of a typical leaf of 'Orange Field'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photograph and following description were grown under conditions which closely approximate commercial production conditions during the summer and early autumn in an outdoor nursery in Rijpwetering, The Netherlands for about two years. During the production of the plants, day temperatures ranged from 12° C. to 24° C. and night temperatures ranged from 4° C. to 12° C.

Botanical classification: *Bistorta amplexicaulis* cultivar Orange Field.

Parentage:

*Female parent.*—Unnamed selection of *Bistorta amplexicaulis,* not patented.

*Male parent.*—Unknown selection of *Bistorta amplexicaulis,* not patented.

Propagation:

*Type cutting.*—Softwood cuttings.

*Time to initiate roots.*—About 30 days at 20° C.

*Time to produce a rooted young plant.*—About 50 days at 20° C.

*Root description.*—Moderately fine, fibrous; dark brown to almost black in color.

*Rooting habit.*—Freely branching; dense.

Plant description:

*Form.*—Perennial. Upright and outwardly spreading plant form; broad inverted triangle; basal branching habit. Moderately vigorous to vigorous growth habit. Flowers arranged on terminal racemes.

*Plant height.*—About 96 cm.

*Plant width.*—About 1.36 meters.

*Lateral branch description.*—Length: About 35.1 cm. Diameter: About 3 mm. Internode length: About 12.1 cm. Strength: Strong. Aspect: Upright to outwardly spreading. Texture: Smooth, glabrous. Color: 144A.

Foliage description:

*Arrangement.*—Alternate, simple.

*Length.*—About 18.2 cm.

*Width.*—About 7.1 cm.

*Shape.*—Narrowly ovate to ovate.

*Apex.*—Apiculate.

*Base.*—Cordate.

*Margin.*—Finely and irregularly serrulate; undulate.

*Texture, upper and lower surfaces.*—Scabrous.

*Venation pattern.*—Pinnate.

*Color.*—Developing foliage, upper surface: Between 144A and 146A. Developing foliage, lower surface: 137C to 138A. Fully expanded foliage, upper surface: Slightly darker than 137A; venation, 145A. Fully expanded foliage, lower surface: 137C to 138A; venation, 145A to 145B.

*Petiole length.*—About 7.9 cm.

*Petiole diameter.*—About 4 mm.

*Petiole color, upper and lower surfaces.*—145A to 145B.

Flower description:

*Flower arrangement and shape.*—Single rotate flowers arranged in terminal racemes; flowers face outwardly to slightly upright. Freely flowering, about 170 flowers per inflorescence.

*Natural flowering season.*—Continuous flowering from late August through October in The Netherlands.

*Flower longevity on the plant.*—About one week; flowers not persistent.

*Fragrance.*—Moderate; sweet.

*Flower buds.*—Length: About 5 mm. Diameter: About 2 mm. Shape: Ovate. Color: 47B.

*Inflorescence size.*—Length: About 11.7 cm. Diameter: About 1.9 cm.

*Flowers.*—Diameter: About 6 mm. Depth (height): About 6 mm.

*Petals.*—Arrangement: Five in a single whorl. Length: About 5 mm. Width: About 2.5 mm. Shape: Ovate. Apex: Bluntly acute. Margin: Entire. Texture, upper and lower surfaces: Smooth, glabrous. Color: When opening, upper surface: 47C. When opening, lower surface: 47B. Fully opened, upper surface: 47C. Fully opened, lower surface: 47C to 47D.

*Calyx.*—No sepals observed.

*Peduncles.*—Length: About 7.3 cm. Diameter: About 2 mm. Aspect: About 10° from vertical. Strength: Strong. Texture: Smooth, glabrous. Color: 144A.

*Pedicels.*—Length: About 3 mm. Diameter: About 0.5 mm. Aspect: About 30° from the stem axis. Strength: Moderately strong. Texture: Smooth, glabrous. Color: 47A to 47B.

*Reproductive organs.*—Stamens: Quantity per flower: About six to eight. Anther shape: Elliptical. Anther length: About 0.5 mm. Anther color: 202A. Filament length: About 3.5 mm. Filament color: 51A to 51B. Pollen amount: Scarce. Pollen color: 202D. Pistils: Quantity per flower: Three. Pistil length: About 3 mm. Stigma shape: Tapering. Stigma color: 51A to 51B. Style length: About 2.8 mm. Style color: 51B. Ovary color: 144B.

*Seed/fruit.*—Seed and fruit production has not been observed.

Disease/pest resistance: Plants of the new *Bistorta* have not been noted to be resistant to pathogens and pests common to *Bistorta.*

Garden performance: Plants of the new *Bistorta* have exhibited good tolerance to rain and wind and have been observed to be suitable for USDA Zones 5 to 9.

It is claimed:

1. A new and distinct *Bistorta* plant named 'Orange Field' as illustrated and described.

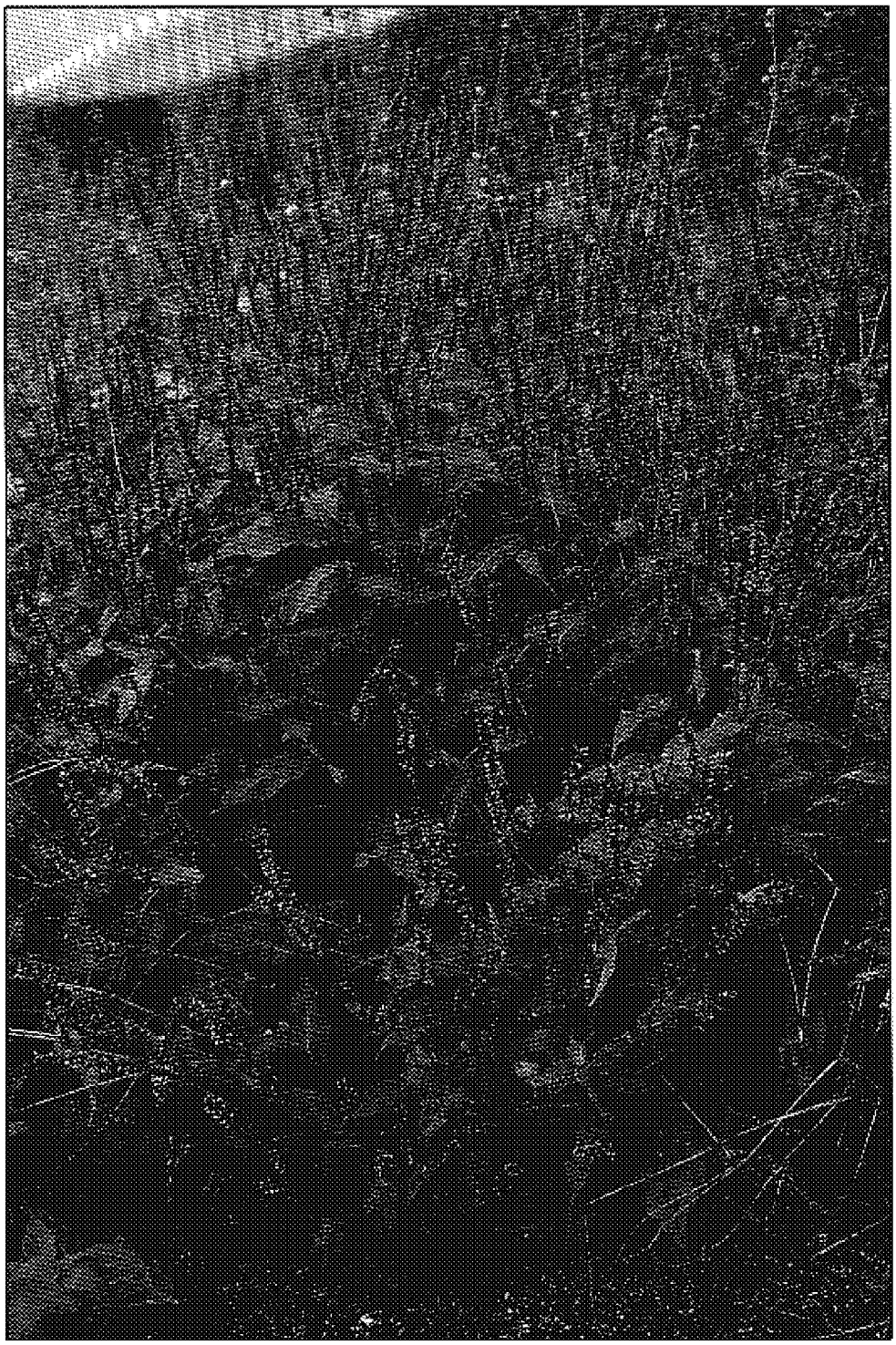

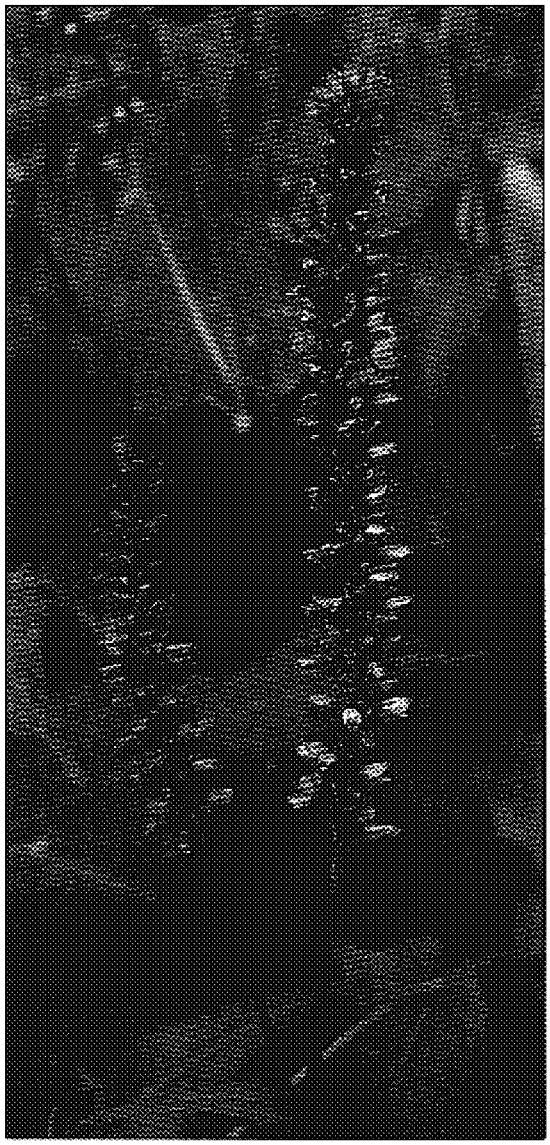
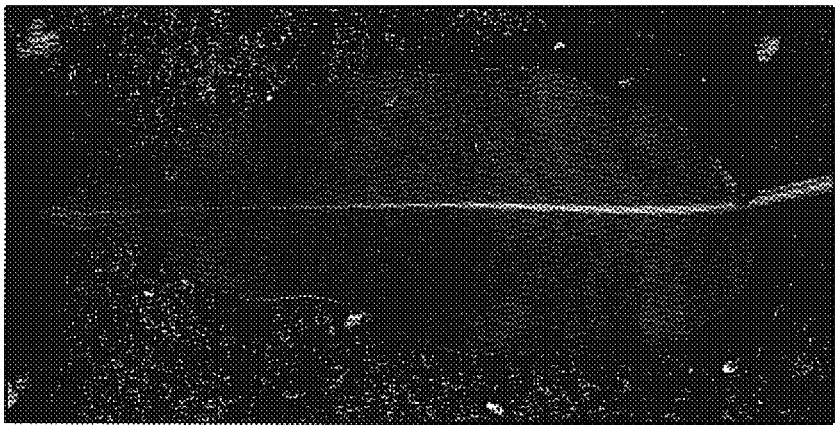

* * * * *